(12) United States Patent
Wilson et al.

(10) Patent No.: US 11,613,725 B2
(45) Date of Patent: Mar. 28, 2023

(54) CULTURE METHODS AND DEVICES FOR TESTING

(71) Applicant: Wilson Wolf Manufacturing, New Brighton, MN (US)

(72) Inventors: John R. Wilson, New Brighton, MN (US); Daniel P. Welch, Zimmerman, MN (US)

(73) Assignee: Wilson Wolf Manufacturing, New Brighton, MN (US)

( * ) Notice: Subject to any disclaimer, the term of this patent is extended or adjusted under 35 U.S.C. 154(b) by 0 days.

(21) Appl. No.: 15/150,381

(22) Filed: May 9, 2016

(65) Prior Publication Data

US 2016/0326478 A1 Nov. 10, 2016

Related U.S. Application Data

(60) Provisional application No. 62/158,583, filed on May 8, 2015.

(51) Int. Cl.
*C12M 1/00* (2006.01)
*C12M 1/24* (2006.01)
*C12M 1/04* (2006.01)

(52) U.S. Cl.
CPC ............ *C12M 23/34* (2013.01); *C12M 23/08* (2013.01); *C12M 23/24* (2013.01)

(58) Field of Classification Search
CPC ...... C12M 23/08; C12M 23/10; C12M 23/12; C12M 23/34
See application file for complete search history.

(56) References Cited

U.S. PATENT DOCUMENTS

| 6,908,767 B2 * | 6/2005 | Bader | B01L 3/5025 |
| | | | 435/286.1 |
| 2005/0106717 A1 | 5/2005 | Wilson et al. | |
| 2005/0170503 A1 | 8/2005 | Falo, Jr. et al. | |
| 2008/0176318 A1 | 7/2008 | Wilson et al. | |
| 2010/0103410 A1 * | 4/2010 | Silbergleit | B01L 3/5085 |
| | | | 356/246 |

(Continued)

FOREIGN PATENT DOCUMENTS

| CN | 1596302 A | 3/2005 |
| CN | 101974487 A | 2/2011 |

(Continued)

OTHER PUBLICATIONS

International Search Report and Written Opinion from PCT Application PCT/US2016/031544, dated Aug. 19, 2016, 7 pgs.

(Continued)

*Primary Examiner* — Lydia Edwards
(74) *Attorney, Agent, or Firm* — Patterson Thuente IP

(57) ABSTRACT

Improved cell culture devices and related methods that overcome the limitations of prior devices and methods, by creating devices that can integrate a variety of novel attributes. These various attributes include the use of gas permeable material and medium volumes that exceed conventional devices as well as compartments that can facilitate the long term study of high density cultures with reduced disruption of the culture environment, the ability to study the migration of items of interest including substances such as chemokine, track the movement of cells, and monitor cell to cell interactions.

19 Claims, 16 Drawing Sheets

(56) References Cited

U.S. PATENT DOCUMENTS

| | | | |
|---|---|---|---|
| 2011/0182870 A1* | 7/2011 | Leen | C12N 5/0636 424/93.71 |
| 2013/0171682 A1 | 7/2013 | Hung et al. | |
| 2013/0295662 A1 | 11/2013 | Cadwell et al. | |
| 2014/0099717 A1 | 4/2014 | Fraker et al. | |
| 2014/0141514 A1 | 5/2014 | Yoon et al. | |
| 2014/0315296 A1 | 10/2014 | Wilson | |

FOREIGN PATENT DOCUMENTS

| | | | |
|---|---|---|---|
| DE | 102008031265 | 1/2010 | |
| DE | 102008031265 A1 * | 1/2010 | C12M 23/34 |
| EP | 0620274 A1 | 3/1994 | |
| EP | 0620274 | 10/1994 | |
| JP | 11-127843 | 5/1999 | |
| JP | 2000184880 | 7/2000 | |
| KR | 10-2010-0117869 A | 11/2010 | |
| KR | 20100117869 | 11/2010 | |
| WO | WO 00/57705 | 10/2000 | |
| WO | WO-2014121289 A2 * | 8/2014 | B01L 3/502 |

OTHER PUBLICATIONS

International Preliminary Report on Patentability from PCT Application PCT/US2016/031544 dated Nov. 23, 2017, 5 pgs.
Extended European Search Report from EP Application 167933453.6 dated Nov. 30, 2018, 7 pgs.

* cited by examiner

A-A

B-B

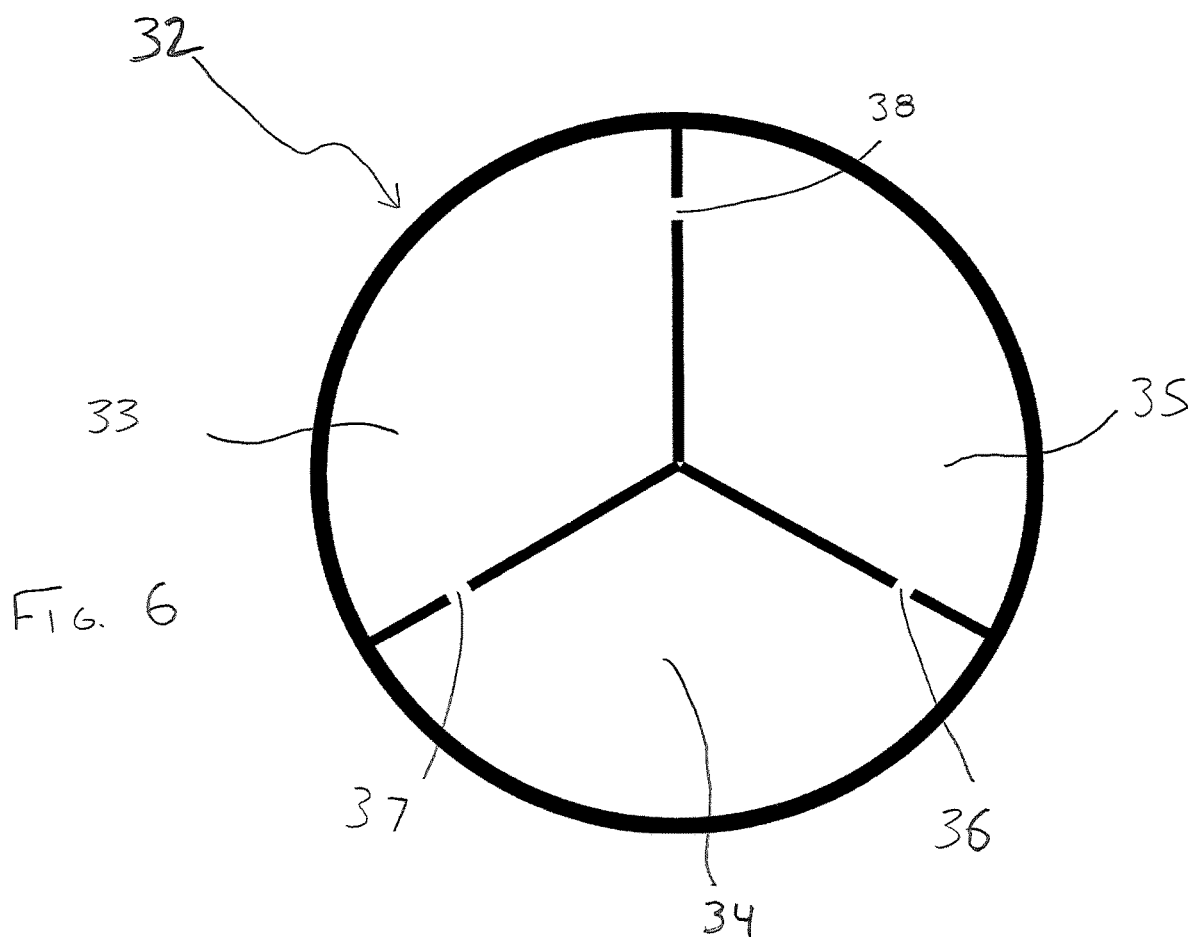

CULTURE METHODS AND DEVICES FOR TESTING

RELATED APPLICATION

The present application claims priority to U.S. Provisional Application No. 62/158,583 filed May 8, 2015, which is hereby incorporated by reference in its entirety.

FIELD OF THE INVENTION

The technical field of the invention relates generally to cell culture devices. More specifically, the present invention is directed to methods and devices that improve the ability for the in vitro study of cell to cell interactions by providing unique geometries that can be used to reduce the number of interventions for feeding, increase cell density, allow gradients to be established by cell secreted products, study the mobility of organisms, and/or improve the ability to assess the ability of T cells to find and/or kill cancer cells.

BACKGROUND OF THE INVENTION

Current static in vitro cell culture devices that are used to culture and/or assess cells that reside at high density are unable to allow a long term culture process without frequent medium exchange to provide nutrients to the cells. This has the detrimental impact of frequently altering the concentrations of various cell secreted signals.

One example of how the design of existing devices is detrimental can be found in the field of T cell therapy where there is a desire to understand how a cytotoxic T cell can migrate to a tumor type environment, attack cancer cells, and persist in the attack. Currently, a typical in vitro approach is to seed cancer cells into a conventional multi-well plate where they gravitate to a three dimensional matrix of some form that is intended to allow cancer cells to grow at high density. Then T cells of the type that can kill the cancer cells are placed into the multi-well plate where their ability to eradicate cancer cells can be assessed. The high number of cells that come to exist in each well imposes a high metabolic demand on the very small quantity of medium in each well. To satisfy the demand, medium must be frequently exchanged. As this occurs, important cell signals that are involved in the killing process are removed and/or diluted by the addition of fresh medium. Hence, the frequently changing culture conditions and can impact the experimental outcomes. Furthermore, as the cancer cells rapidly expand in quantity, the ability to exchange the medium frequently enough to satisfy their metabolic demand is lost entirely, limiting the duration of experiments to just a few days.

A common way of avoiding that problem is to use Severe Combined Immunodeficient (SCID) mice. To conduct an evaluation, cancer cells are introduced into or induced within the mouse. Subsequently, T cells are introduced into the mouse. The nutrient demands of the cells are supported by the mouse for a much longer time period than can be undertaken using conventional in vitro tools and frequent alterations to cellular conditions inherent to in vitro devices are avoided. However, use of mice is highly controlled and mouse to mouse variability is difficult to predict.

Certain embodiments disclosed herein provide more efficient cell culture devices and methods that overcome the limitations of prior devices and methods, by creating devices that can integrate a variety of novel attributes.

SUMMARY OF THE INVENTION

It has been discovered that in vitro devices with unique geometries can provide a superior alternative to existing devices for long term culture and/or when migration of cells or substances within the culture is desired. The novel static devices and methods for use do not require medium mixing equipment, medium perfusion equipment, or gas pumping equipment to function.

Certain embodiments disclosed herein provide an improved cell culture environment that allows cells, such as cancer cells, to grow at high density without need to supplement nutrients as frequently as existing high density static cell culture devices. This can be beneficial for example when there is a desire to study the ability of T cells to attack cancer cells and persist in that effort by allowing the process to continue without disrupting the process to supplement nutrients for a much longer period of time than existing state-of-the-art devices allow. By less frequent interruption of the process to feed the cultures, including the possibility of no interruption at all, there are fewer variables to consider when assessing outcomes.

Certain embodiments disclosed herein describe improved geometry relative to existing static cell culture devices that allows substances and/or cells within the device to migrate throughout the device. This geometry can be altered to control the way that components within the medium to travel between compartments and cells within the device to travel between compartments. By altering the geometry and materials to increase nutrient and oxygen supply, long term study of any process that includes cells can be accomplished.

Such embodiments can be used to assess the ability of cells emit signals on a long term basis, to respond to signals, and/or to migrate to the source of signals. For example, cancer cells cultured at high density can become a source of chemokine signals, the signals can move through a maze of compartments and eventually reach T cells within the device causing them to respond by moving through the maze to find the source. Once the T cells find the cancer cells are the source, they can initiate killing of the cancer cells and persist in that effort. The geometry can be appropriately structured to allow such a process to proceed without disruption from feeding or from physical forces within the medium than can result from moving the device. The device can also be structure to allow the process to be visually monitored.

Such embodiments can allow the capacity of genetically engineered T cells to find cancer targets, kill the cancer targets and persist in killing the cancer targets. Device geometry can allow comparison of T cell populations with different genetically engineered characteristics to be compared. They can allow an assessment of how well genetically T cells can react to differing types of cancer cells. They can also allow an assessment of how well native T cells react to tumor associated antigens.

Such embodiments can change the capacity of substances of interest to migrate between compartments, can change the path by which they migrate and can open or close the path by which they migrate.

Certain embodiments disclosed herein provide more efficient cell culture devices that can integrate a variety of novel attributes. Representative attributes can include the use of gas permeable material and medium volumes that exceed conventional devices as well as compartments that can facilitate the long term study of high density cultures with reduced disruption of the culture environment, the ability to study the migration of items of interest including substances such as chemokine, track the movement of cells, and monitor cell to cell interactions.

BRIEF DESCRIPTION OF THE DRAWINGS

FIG. 6 shows a circular configuration of the present invention which included compartments that are pie shaped.

FIG. 12B compares cancer cell growth of the prototypes vs. the SCID mice vs. the AlgiMatrix™ 3D Culture System plate.

DETAILED DESCRIPTION OF THE INVENTION

Figure 1:
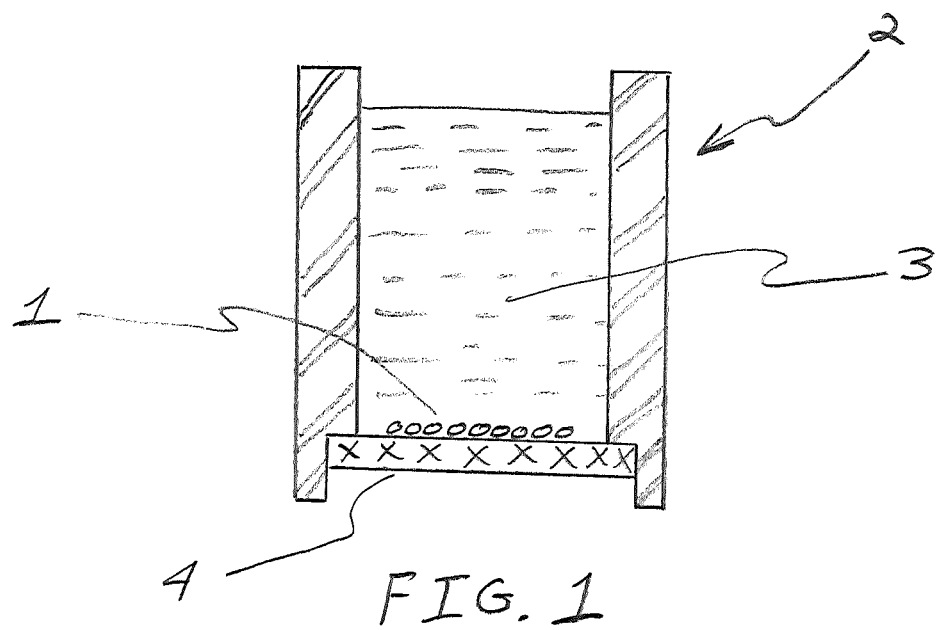
FIG. 1 shows a cross-sectional view of an embodiment that is configured to allow long term culture that can be of benefit for various cell culture applications including the study of the ability for T cells to kill cancer cells and persist in that effort.

FIG. 1 shows a cross-sectional view of an embodiment of the present invention that depicts a device that does not integrate medium mixing equipment, medium perfusion equipment, or gas pumping equipment and that can be used to culture cancer cells at high density and study the ability of T cells to kill cancer cells and persist in that effort. Cancer cells 1 reside at the bottom of static cell culture device 2. The top is not shown but can be as simple as a cover traditionally associated with multiple well plates or can be more sophisticated including closed and configured for automated access. Medium 3 resides within cancer cell culture device 2. Bottom 4 of the device is comprised of gas permeable material, preferably silicone. Modifying the surface that cells will contact on the bottom of the compartment, such as by texturing, can be undertaken to allow the cancer cells to exist at a high density state in order to simulate a tumor. Surface texture can take the form of grooves, pockets, roughened areas, and the like. In essence, when bottom surface is not smooth, for each square centimeter of footprint relative to a device with a smooth surface, it can increase the surface area that cancer cells can come in contact with and facilitate an increase in cells per square centimeter of the compartment bottom. A matrix can also be used for the culture of cells at high density or more natural physical configuration. A matrix is often used to culture cells in what is commonly referred to as three dimensions. The matrix can be attached to the bottom surface but does not need to be attached to the bottom surface. Matrix material can consist of any material known by artisans to allow cells to be culture in a state that allows cells to reside in close contact and/or integrate within the matrix, including naturally occurring or synthetic material such as AlgiMatrix™, collagen, fibronectin, plastic, sintered ceramic are among the many choices available. Such material, when the bottom is gas permeable, should strike a balance between allowing cells to reside in close contact (such as when cancer cells are used to simulate a tumor) and allowing oxygen to reach the cells. Thus, preferably the matrix is not a solid substance.

This embodiment overcomes the limitations of traditional in vitro culture devices such as the AlgiMatrix™ 3D Culture System 24-well plate (Gibco Catalog No. 12684-023). By providing superior oxygenation via the gas permeable bottom and providing a large volume of medium T cells can be added to the device and long term assessments of their cancer killing capacity can be made. By allowing the ratio of the medium volume to footprint of the bottom to exceed that of the AlgiMatrix™ 3D Culture System 24-well plate, the device can function for longer durations with many advantages as will be shown. The footprint of the bottom is the determined by calculating the surface area of the bottom as if the bottom surface was smooth, thereby avoiding the inclusion of texture, growth matrices, or other forms of adding surface area. Preferably, the medium volume to bottom footprint ratio exceeds that of the AlgiMatrix™ 3D Culture System 24-well plate. Hence, in the preferred embodiment, medium volume to bottom footprint ratio is 2, 3, 4, 5, 6, 7, 8, 9, 10, 11, 12, 13, 14, 15 or any number in between. The bottom is preferably comprised of silicone. To improve the ability to assess cellular activity within the device, particularly by way of fluorescent detection, at least the walls should be tinted in color. The bottoms can preferably also be tinted in color or both the walls and the bottoms can be tinted in color.

Figure 2A:
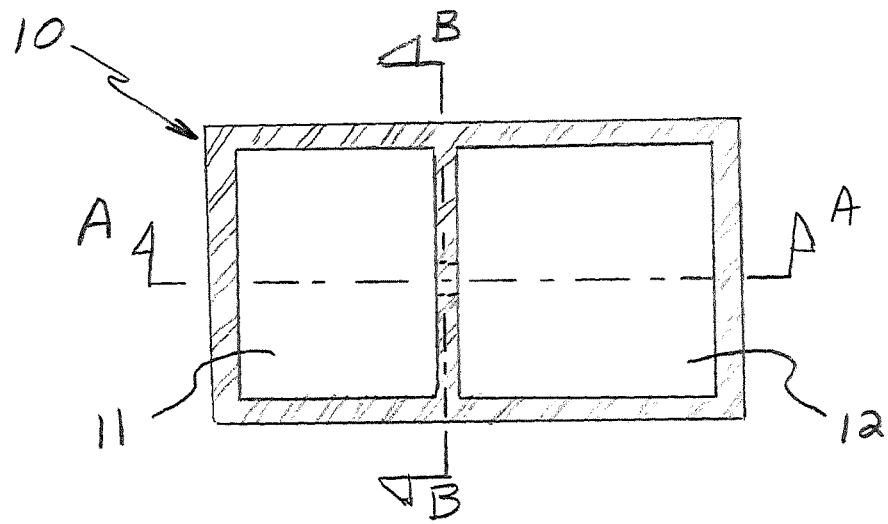
FIG. 2A, FIG. 2B, and FIG. 2C show various views of a compartmentalized device which includes two compartments.
Figure 2B:
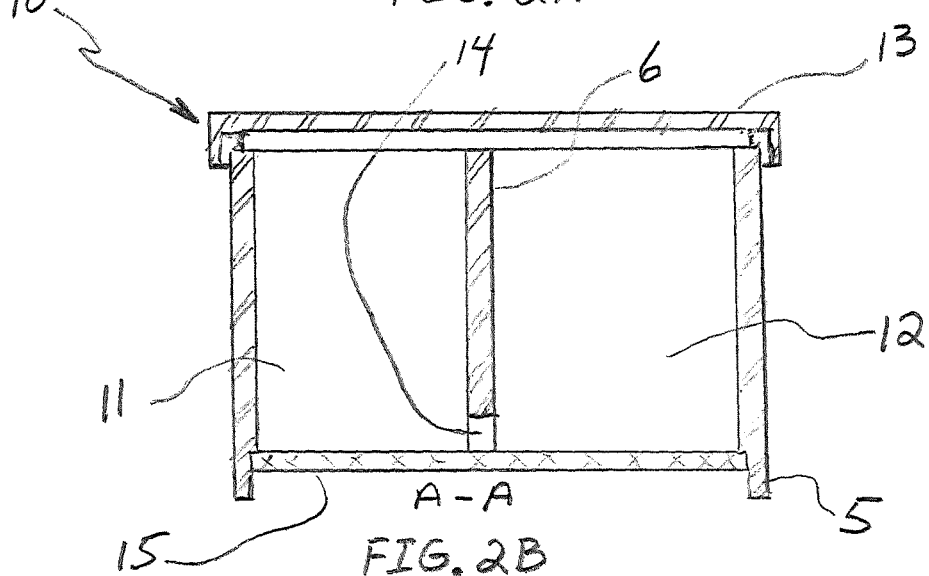
Figure 2C:
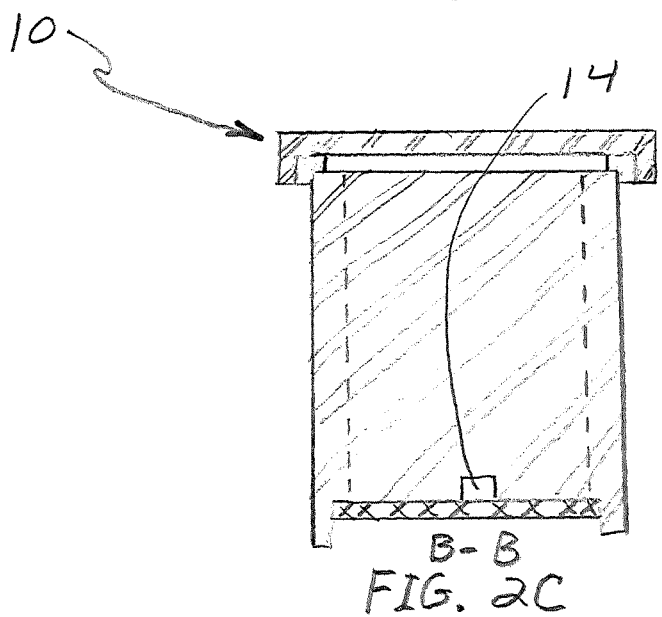

FIG. 2A shows a top view of compartmentalized device 10, which includes two compartments. For clarity, the top is removed. Although the perimeter of each compartment is shown as square, they can be any shape and each compartment need not have the same shape or surface area. As best shown in FIG. 2B, which is a cross-sectional view A-A of FIG. 2A, passage 14 connects compartment 11 to adjacent to compartment 12. In this depiction, the compartments are shown with top 13. Top 13 can be similar to the top of a traditional multiple well plate. The bottom of the compartments can be gas impermeable or gas permeable. If gas permeable, the material should be preferably liquid impermeable. By making bottom 15 of each compartment gas permeable, top 13 need not allow a gap for gas transfer to the compartments and can be sealed to the device to minimize contamination risk. In the depiction of FIG. 2B, top 13 is shown elevated in a similar manner as with the top of a conventional multiwell plate. Feet 5 can be used to elevate the bottom of the compartments. This can serve more than one purpose. For example, if there is a desired to assess the contents of the compartment by way of the bottom (such as by use of an inverted microscope), the feet can prevent the bottom from becoming scratched or otherwise diminished in its ability to facilitate such an assessment. If there is a desire to use gas permeable material for the bottom of one of more compartments, feet can elevate the bottom to facilitate the ability of ambient gas to make unforced contact with the gas permeable material. The bottom, if gas permeable, should be in contact with ambient gas that does not need to be pumped or otherwise placed in forced motion to contact the gas permeable material. Artisans are encouraged to review U.S. Pat. No. 9,255,243, which is hereby incorporated by reference in its entirety, to learn more about techniques to hold the gas permeable material in a horizontal plane while allowing ambient gas to make passive, unforced contact with the material. FIG. 2C shows section B-B of FIG. 2A. In this depiction, passage 14 is an opening in the wall that separates adjacent compartments 11 and 12. Passage 14 can be any opening that allows the contents of one compartment to communicate with another.

Figure 3A:
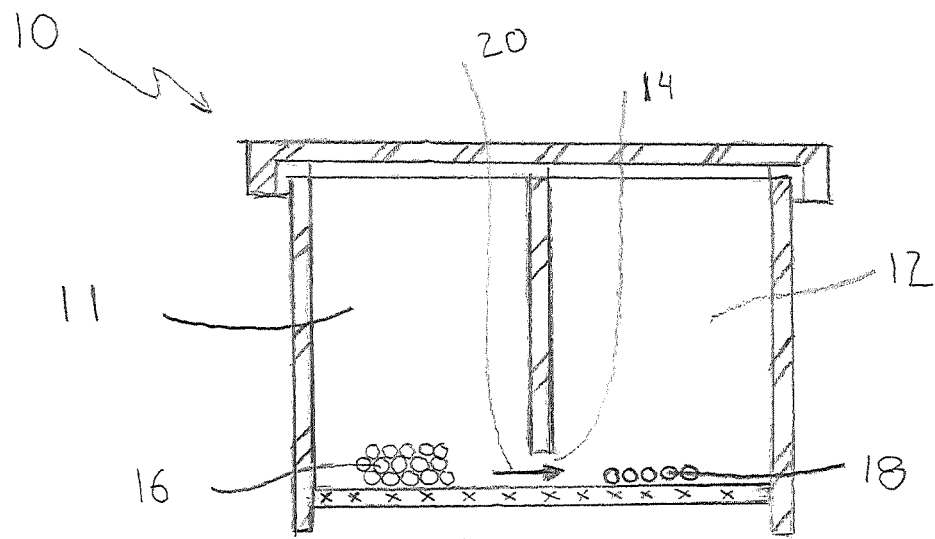
FIG. 3A, FIG. 3B, and FIG. 3C show an example of how compartmentalized device, previously described and shown in FIG. 2A, FIG. 2B, and FIG. 2C, can be used.
Figure 3B:
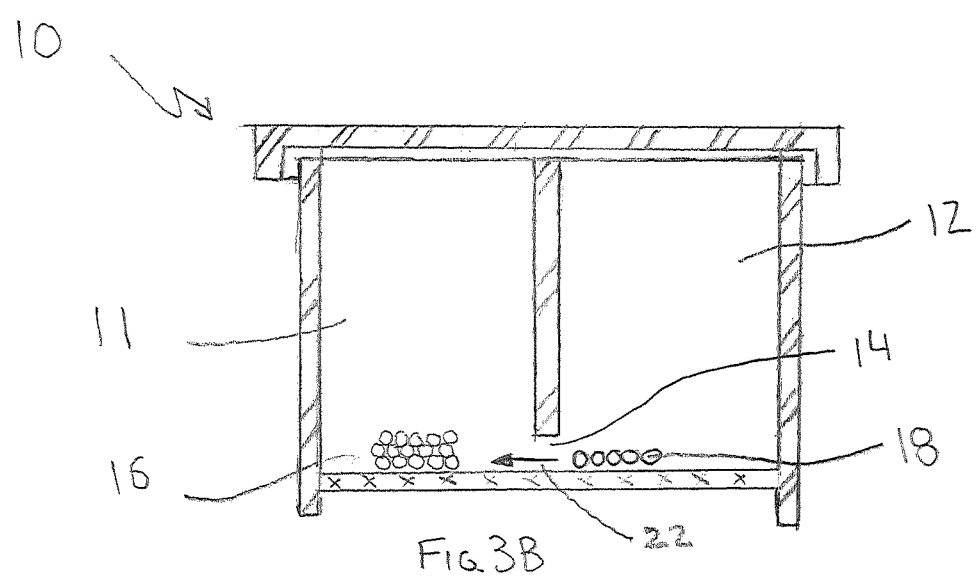
Figure 3C:
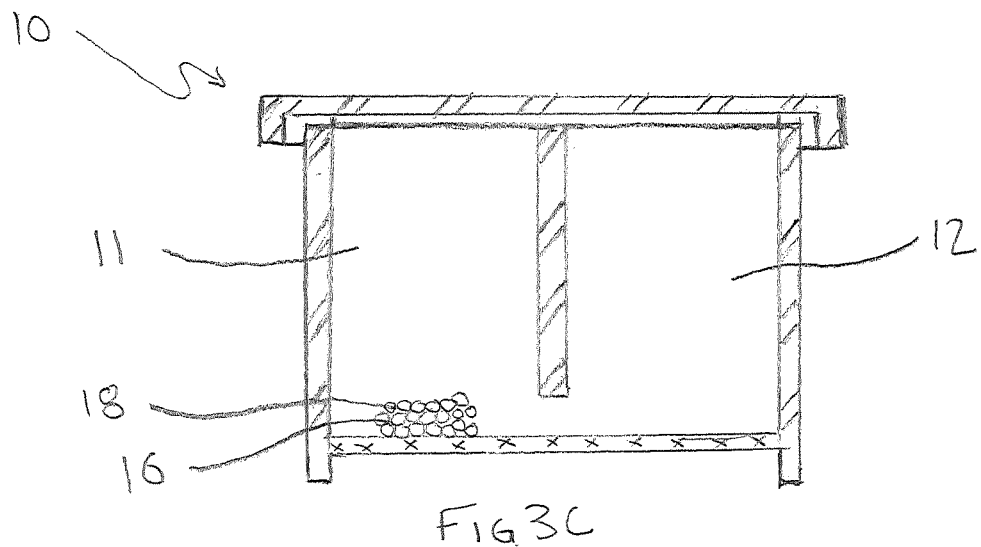

FIG. 3A, FIG. 3B, and FIG. 3C show an example of how compartmentalized device 10, previously described and shown in FIG. 2A, FIG. 2B, and FIG. 2C, can be used. This device configuration allows assessment of the capability of T cells to recognize chemokine gradients, follow the gradient, find cancer cells, initiate cancer cell killing, and persist in that effort. As shown in FIG. 3A, cancer cells 16 reside in compartment 11 and T cells 18 reside in compartment 12. Arrow 20 shows the direction that chemokine secreted by cancer cells 16 moves through passage 14 as it travels from an area of higher concentration to an area of lower concentration. Arrow 22 of FIG. 3B shows the direction that T cells 18 migrate through passage 14 as they seek the source of the chemokine, moving from an area of lower chemokine concentration to an area of higher chemokine concentration. FIG. 3C shows how T cells 18 have migrated into compartment 11 in search of cancer cells 16. For clarity, the presence of medium has not been shown. This device configuration allows assessment of the capability of T cells to recognize chemokine gradients, follow the gradient, find cancer cells, initiate cancer cell killing, and persist in that effort.

A wide variety of design attributes can be used to alter performance of the device and optimize it for a particular application. Examples can help explain how design attributes can be altered to make the performance of the device well suited to specific applications. One such example is an application in which the user of the device seeks to assess the capacity of T cells to find and kill cancer cells. In this application, one important aspect of the device is the geometry of the bottom of each compartment. In the compartment where cancer cells reside, they preferably grow to high density in order to simulate a tumor. In the areas of the device where cancer cells do not reside, a design goal should be to create an environment where the T cells are not impeded from migrating to the cancer cell location. Therefore, the surface that T cells will migrate across should be flat and not textured. A smooth surface finish that has an even and regular consistency, free from projections, lumps, or indentations that are easily perceptible is preferred. A surface finish of Society of Plastic Engineers (SPE) surface finish number 2 more preferred, and a SPE surface finish number 1 is most preferred. It is also preferred that the surfaces across which cells will migrate are generally horizontal when the device is in use to minimize the possibility of cells having to travel uphill or the possibility of cells gravitating downhill. Either of these conditions could mislead a researcher into thinking the T cells are moving faster or slower than they actually would have if the surface were horizontal. The intention is for the T cells to move by chemokine stimulation so they can be assessed in terms of their capacity to move towards, and find, cancer cells. Therefore, the design intent is to minimize unwanted forces that can act to move the T cells to the cancer cells or diminish the capacity of the T cells to migrate to the cancer cells. Skilled artisans should be aware that creating a perfectly horizontal surface is not likely, but surfaces similar to what are common in a traditional multiple well plate or commercially available G-Rex® devices are suitable. Unwanted forces not only include the impact of gravity, they include the momentum of medium when the device is moved. It will be described in more detail how various passage designs and passage locations can minimize the effects of momentum. Further, when cell migration is desired, material that is expected to make contact with cells during their anticipated migration path is preferably hydrophobic so that it can facilitate cell migration. Stated differently, when cell migration is desired, the material in contact with the migrating cells should not be one that cells can attach to.

The bottom of each compartment may be made of any material used in cell culture devices and need not be gas permeable. Such materials include polystyrene of the thickness typically found in traditional multiwell plates for example. However, we have found that the use of gas permeable materials in the bottom can create advantages as will be further described. Such material can be any membrane, film, or material used for gas permeable cell culture devices, such as silicone, flouroethylenepolypropylene, polyolefin, polystyrene, and ethylene vinyl acetate copolymer. Those skilled in the art will recognize that the gas permeable material should be selected based on a variety of characteristics including gas permeability, moisture vapor transmission, capacity to be altered for desired cell interaction with cells, optical clarity, physical strength, and the like. A wide variety of information exists that describe the types of gas permeable materials that have been successfully used for cell culture. Silicone is s preferred choice. It has excellent oxygen permeability, can allow optical observation, is not easily punctured, typically does not bind the cells to it, and can be easily fabricated into a wide variety of shapes suitable for the present invention.

The height of the walls can dictate how much medium is allowed to reside in the device. Adding medium provides a larger source of substrates, and a larger sink for waste products. By increasing wall height and increasing the volume of medium that can exist in a compartment, it can have the effect of reducing feeding frequency, thereby reducing shifts in the concentration of solutes and substances in the medium. It can also have the effect of increasing the number of cells residing per square centimeter of device footprint.

Figure 4:
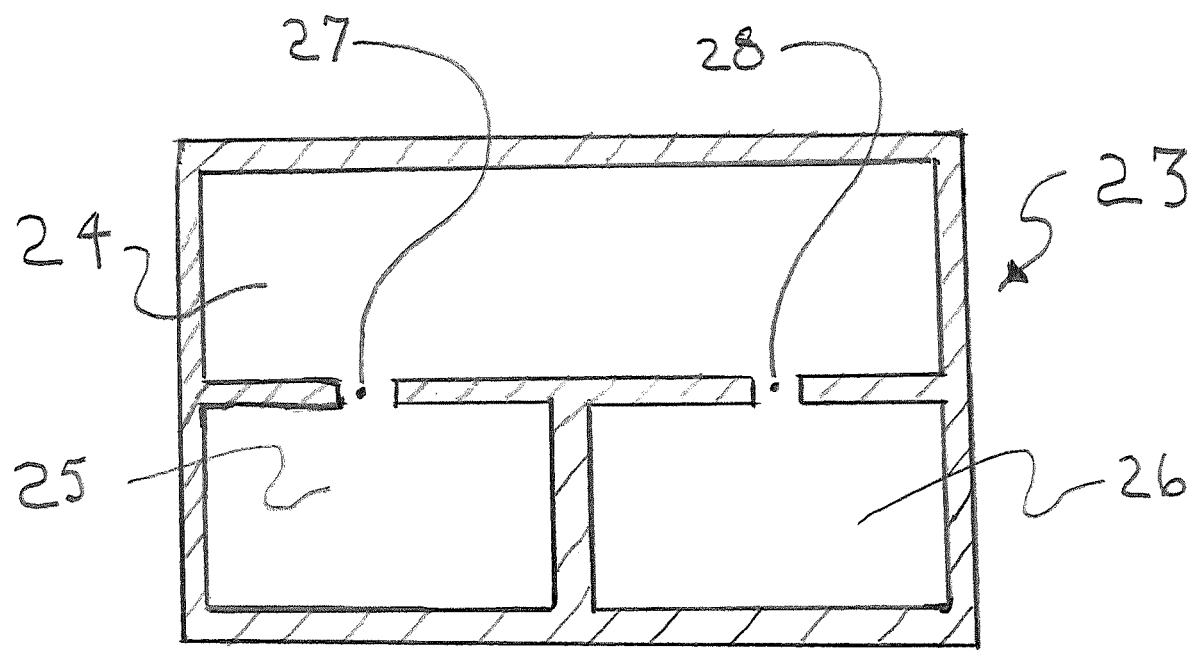
FIG. 4 shows a top view of a compartmentalized device with three compartments.

There may be a desire to use more than two compartments. FIG. 4 shows a top view of a compartmentalized device with three compartments. For clarity, material not related to the boundaries of the compartments and the passages between compartments is not shown. This configuration can be used to assess the ability for differing populations of T cells to recognize various types of cancer. For example, cancer cells from one type of cancer can reside in compartment 24 of compartmentalized device 23. A particular population of T cells can reside in compartment 25 and a different population of T cells can reside in compartment 26. As cancer cells secrete chemokine signals, the type of T cells best able to respond and migrate to the cancer cells can be observed. Such an evaluation can be useful for example when evaluating T cell populations that have each been conferred with different attributes by genetic engineering. With this configuration, the genetically engineered T cell population that migrates most quickly to the cancer cells can help with the assessment of how well the genetically engineered attributes are expected to function in vivo. The killing capacity can also be assessed.

Preferably, compartment 25 and compartment 26 are created with the thought of providing them we identical geometry and material so that any differences in T cell response are attributable to the T cells and not the geometry or the type of material within the compartments. Hence, identical geometry and material between compartment 25 and compartment 26 is preferred. A key attribute is the configuration of passage or passages between compartments. Skilled artisans should be advised that there need not be just one passage between compartments. In this depiction, just one passage is shown for clarity. Preferably the passage, or passages, between compartment 25 and compartment 24 are configured with identical geometry to the passage, or passages, between compartment 26 and compartment 24. An important consideration when designing the passage(s) is to place them in the same relation to compartment 24. For example, in FIG. 4 passage 27 is in the center of the wall that separates compartment 25 from compartment 24 and passage 28 is in the center of the wall that separates compartment 26 from compartment 24. Assuming the cancer cells and T cells are uniformly distributed throughout their respective compartments, this helps ensure chemokine signals reach the T cells at about the same time with about the same concentration of the signal.

An alternative application for the geometry shown in FIG. 4 would be to place the T cells in compartment 24 and then two different types of cancer cells with in compartments 25 and compartment 26. In this configuration the T cells can be evaluated to their response and movement towards the different cancer types. Such an application may be particularly beneficial when T cell populations comprised of T cells that recognize more than one tumor associated antigens are assessed for their ability to recognize different types of tumor like cancer cell populations. Also, for any embodiment herein, when assessing cancer recognition and killing capacity, actual tumor fragments can be used in lieu of cancer cells.

Figure 5A:
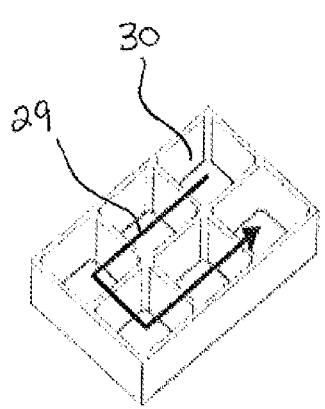
FIG. 5A, FIG. 5B, and FIG. 5C each show a perspective views of alternative configurations of a six compartment device of the present invention.
Figure 5B:
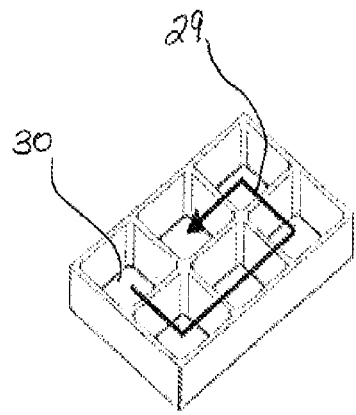
Figure 5C:
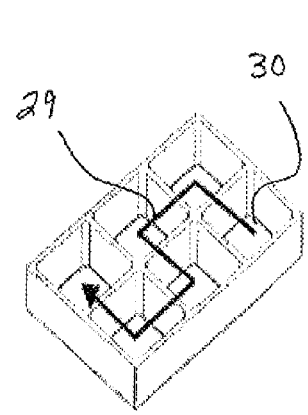

Any number of compartments can be including one, two, three, four, five, six, and more can be used. As previously stated, the compartment shape is not limited to square or rectangle. FIG. 5A, FIG. 5B, and FIG. 5C each show a perspective views of alternative configurations of a six compartment device of the present invention. The passage(s) between various compartments can be configured in a variety of patterns to allow migratory substances and/or microorganisms such as chemokine and/or cells to travel between compartments. For each configuration shown, arrow 29 indicates the path of migration when the migration begins in compartment 30 and ends where the arrowhead of arrow 29 terminates. Specific passage geometry is not shown in FIG. 5A, FIG. 5B, and FIG. 5C in order to focus on the point that the location of passages can create various paths among compartments. Some paths, relative to others, can minimize the momentum of medium when the device is moved and thereby minimizes the potential for signals to be carried from compartment to compartment by the movement of liquid during device handling. In this depiction, at some point each arrow takes one or more turns. Hence, when created a device configuration with one well expected to be the source of a cell secreted signal and one well expected to contain cells that respond to the source of the cell secreted signal, the passages between those particular wells are preferably not entirely fully aligned. Preferably the pathway for signal has at least one turn as for example shown in FIG. 5A, more preferable more than one turn as shown for example in FIG. 5B, and even more preferably makes a turn in each compartment that is not a source of the signal or a final destination of the signal as shown for example in FIG. 5C.

FIG. 6 shows a circular configuration of the present invention which included compartments that are pie shaped. For clarity just an outline of the compartments and passages are shown. Within compartmentalized device 32, compartment 33 is connected to compartment 34 by passage 37, compartment 34 is connected to compartment 35 by passage 36, and compartment 35 is connected to compartment 33 by passage 38. In this configuration, each compartment is in contact with its adjacent compartments by passages.

Figure 7:
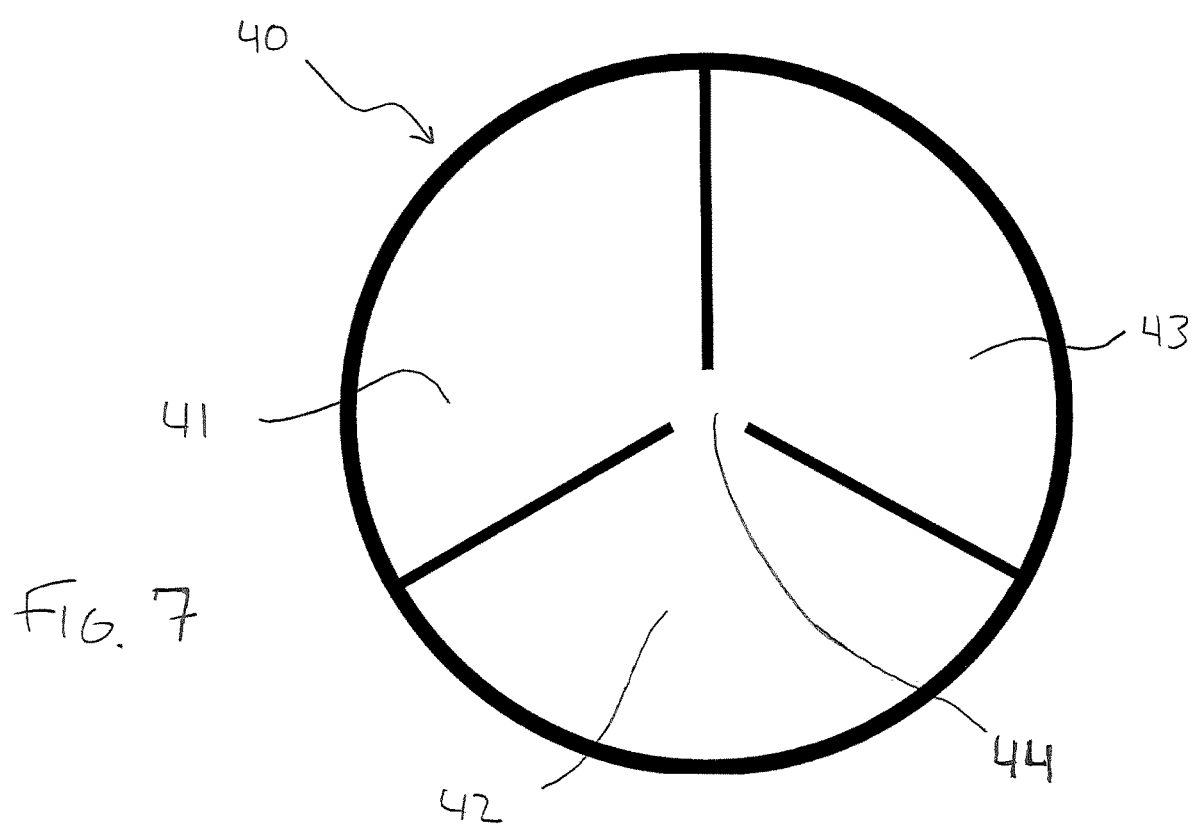
FIG. 7 shows a circular configuration of the present invention which included compartments that are pie shaped.

FIG. 7 shows a circular configuration of the present invention which included compartments that are pie shaped. For clarity just an outline of the compartments and passages are shown. Within compartmentalized device 40, compartment 41, compartment 42, and compartment 43 are all connected by passage 44. In the case where it is deemed advantageous to have more than two compartment connected by just one passage, this is one illustrative embodiment showing how that can be achieved.

Figure 8:
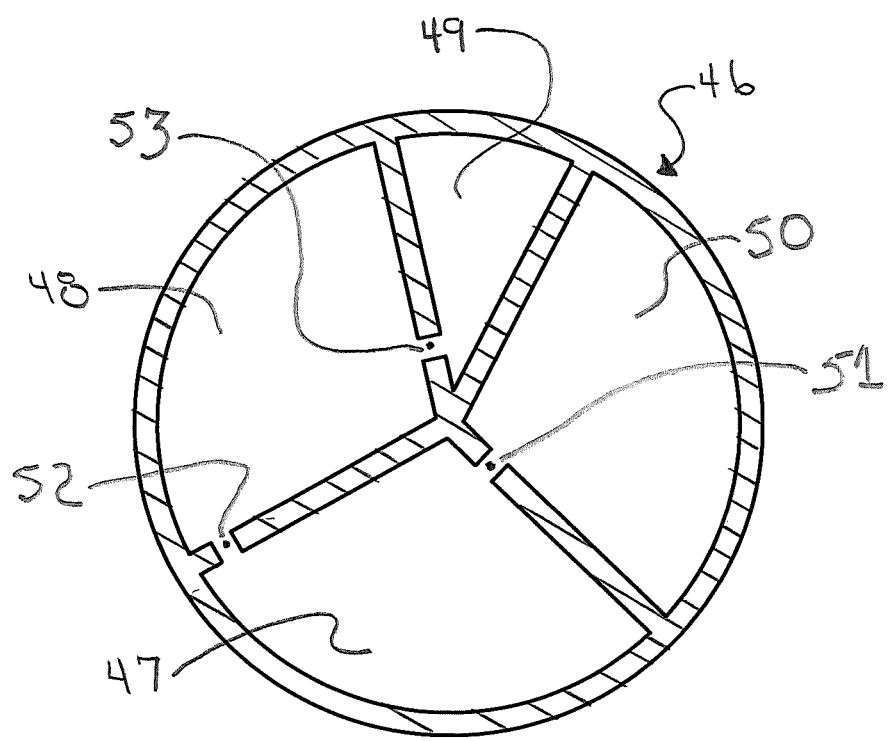
FIG. 8 shows an embodiment of the compartmentalized device that is subdivided into compartments that are not symmetrical.

FIG. 8 shows an embodiment of the compartmentalized device that is subdivided into compartments that are not symmetrical. Compartmentalized device 46 includes compartment 47, compartment 48, and compartment 49, and compartment 50. Passage 51, passage 52, passage 53 allow transport of substances between compartment 49 and compartment 50. The locations of the passages relative to the center point of the device vary and can increase the migratory pathway without increasing the size of the device footprint.

The shape, quantity, and orientation of the passage(s) that separate compartments can impact performance. Their design should strike a balance between allowing elements within the contents of the device to pass from compartment to compartment with the need to minimize physical forces from propelling such elements from compartment to compartment. For example, if T cells are being monitored for their capacity to find cancer cells, the very act of moving the device to monitor such an event should not facilitate that event. Of note, the number of passages between compartments need not be limited to just one. One, two, three, four, five, six or any number of passages can be used. The design of the passage, or passages, between wells can also affect T cell migration. For example, if the device is moved from a flow hood to an incubator, the capacity of medium to move through the passage from one compartment to the next should be minimized to prevent the momentum of medium from carrying T cells from one compartment to another or from carrying cancer cells from one compartment to another. This can be accomplished in a variety of ways.

Figure 9:
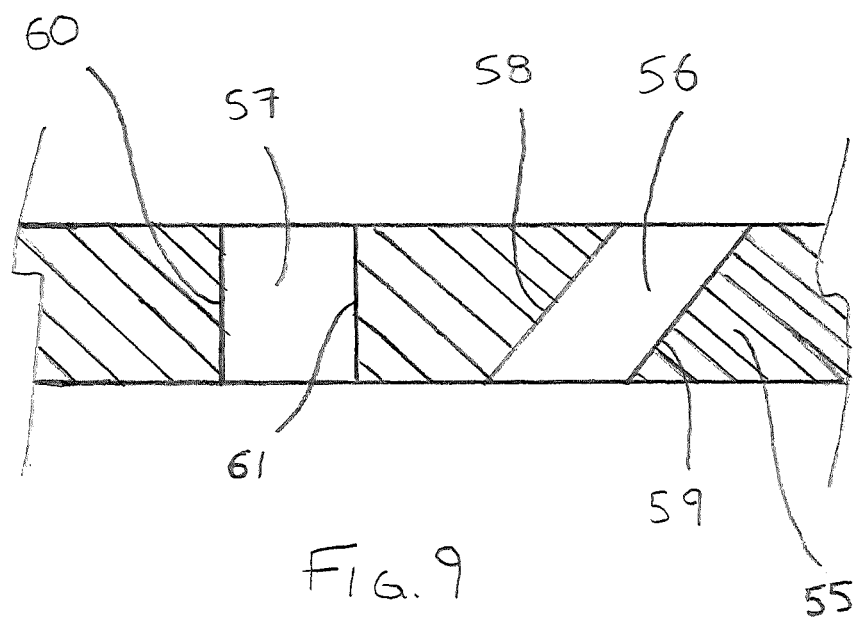
FIG. 9 shows one configuration of the passage that can be used to minimize the movement of medium from compartment to compartment.

FIG. 9 shows one configuration of the passage that can be used to minimize the movement of medium from compartment to compartment. Wall 58 and wall 59 of passage 56 do not cut a perpendicular path through compartment wall 55. On the other hand wall 60 and wall 61 of passage 57 do cut a perpendicular path through compartment wall 55. Although either passage can be used, in this case passage 56 can be used to create resistance to medium momentum during device handling.

Figure 10:
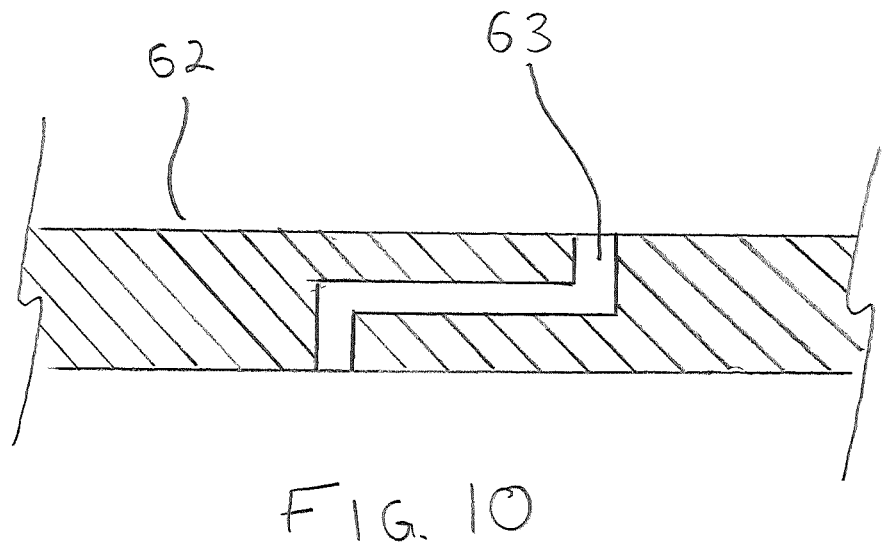
FIG. 10 shows another configuration of how the passage that can be used to minimize the movement of medium from compartment to compartment.

FIG. 10 shows another configuration of how the passage that can be used to minimize the movement of medium from compartment to compartment. Passage 63 does not cut a perpendicular path through compartment wall 62. To the contrary passage 63 includes two right angle turns within compartment wall 62. Artisans are encouraged to recognize that at least one turn of any angle in a passage can be used to limit the force of momentum from driving substances through a compartment wall.

Figure 11:
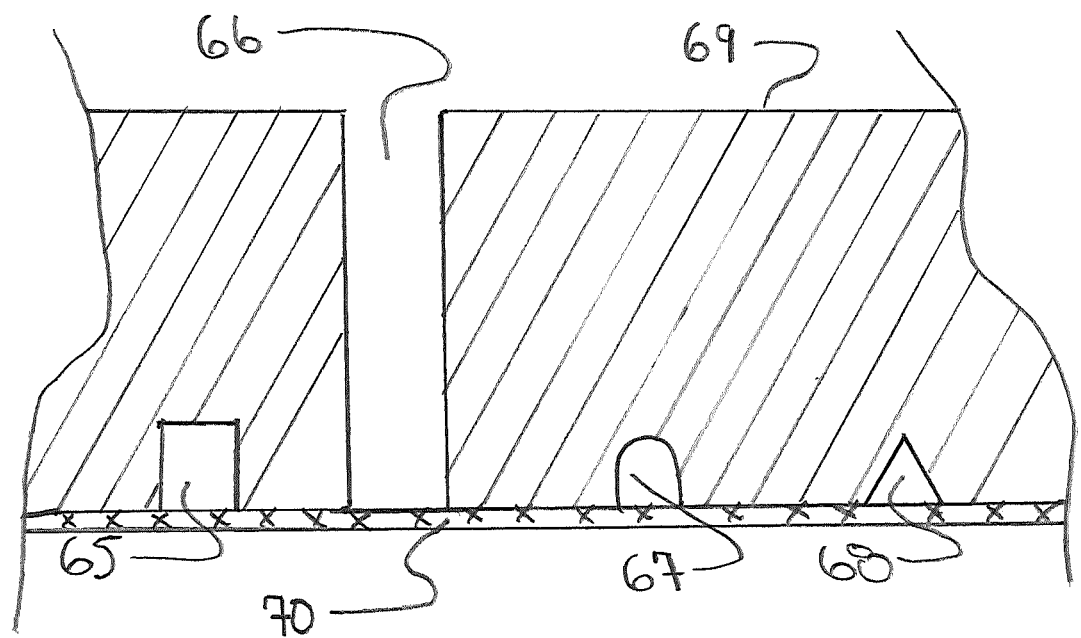
FIG. 11 shows how passages can be of any shape and can remove any amount of material from a compartment wall that is desired for a particular application.

FIG. 11 shows how passages can be of any shape and can remove any amount of material from a compartment wall that is desired for a particular application. For example, passage 65 has a rectangular, passage 67 has a rectangular shape with a circular shape at its top, and passage 68 has a triangular shape. Passage 66 is a slot that forms a complete break in compartment wall 69. Compartment wall 69 is mated to bottom 70. When compartment wall is molded as one piece with bottom, it may be advantageous to mold a slot that completely breaks the compartment wall. Then a second component can be attached to the compartment wall to block any portion of the slot that is desired. In this case the compartment wall would include a first wall with an opening and a wall component that restricts the opening. The size of the first opening would be reduced by the wall component. Artisans are encouraged to recognize that more than one passage can be used in a given compartment wall and when so toing, each passage can have a different shape and/or size and/or cross-sectional area to suit any given application.

Passages need not be permanently open. They can include a closure that prevents contents from a compartment from passing through the wall. The closure can be opened when it is desirable to allow contents of a compartment to pass through the passage.

For experiments that include a desire to monitor the fluorescence of a substance or item, making walls and/or the bottom of a compartment such that they are not optically clear can provide a benefit. If made of plastic, colorant should be included in the material. The choice of materials for walls and the bottom is also a consideration. In a preferred method of fabrication, the walls and the bottom are fabricated with silicone. In a more preferred method of fabrication, walls and the bottom are injection molded and are adjoined during that process. The use of colorant in the silicone can be beneficial when and application may include the monitoring of fluorescent markers. It can also be practical to over mold a silicone bottom onto compartment walls that are tinted. Thus, the silicone bottom can be optically clear while the walls are tinted. The invention will be further described with reference to the following non-limiting Examples.

Example 1

The novel device provides benefits for the study of cancer cells when compared to a commonly used conventional in vitro device and when comparted to SCID mice.

Evaluations were undertaken to determine if the compartmentalized device of the present invention could maintain cancer cells in a superior manner to a standard in vitro tool that is typically used to cultivate cancer cells. The evaluations also made comparison to the in vivo culture of cancer cells in a SCID mouse.

A prototype of one embodiment of compartmentalized device was created. The device in which cancer cells were placed had square bottom with a surface area of 12 $cm^2$ that was comprised of silicone with a thickness between 0.008 to 0.012 inches. The walls of the compartment were of a height that allowed medium to reside at a height of 5 cm and medium resided directly above the bottom.

Figure 12:
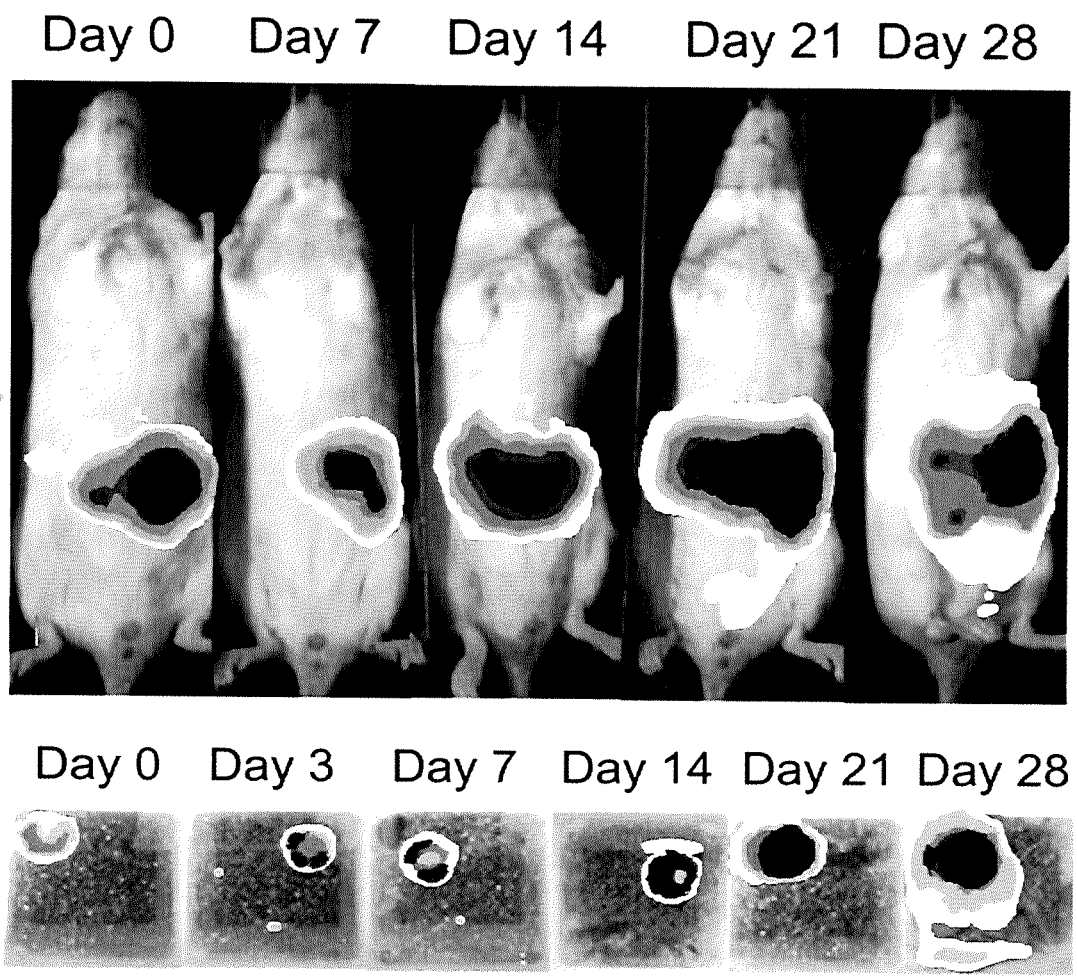
FIG. 12 shows a representative example of cancer cells proliferating in a SCID mouse and in the prototype as represented by the bioluminescence signal progressively increasing over a 28-day time period.
Figure 13:
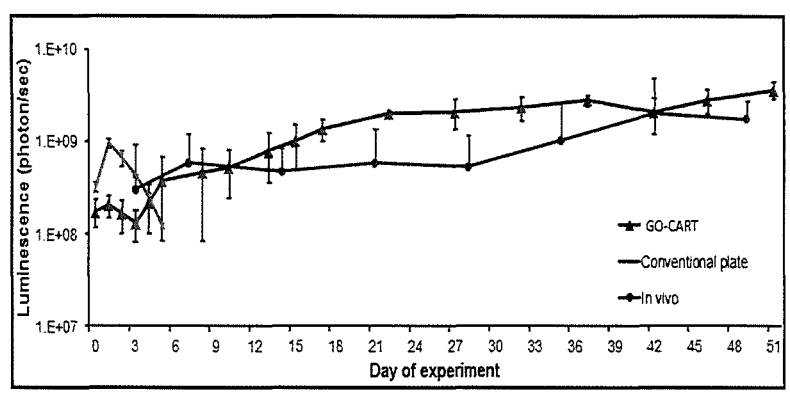
FIG. 13 shows cancer cells cultured in the conventional AlgiMatrix™ 3D Culture System plate quickly exhausted their nutrient supply and died by day 7.

To confirm that this novel approach could support long-term tumor growth, the prototype was comparted to the AlgiMatrix™ 3D Culture System 24-well plate (Gibco Catalog No. 12684-023) and to SCID mice, which are commonly used for cancer cell studies. To initiate the comparison, each of six wells of an AlgiMatrix™ 3D Culture System 24-well plate received $1 \times 10^6$ CAPAN-1 cancer cells. Approximately 24 hours later, after the cancer cells had engrafted into the AlgiMatrix™ bioscaffold, three scaffolds were removed and distributed separately to each of three prototypes. Thus each prototype now had one AlgiMatrix™ bioscaffold engrafted with cancer cells. Each prototype received 60 ml of medium, and each of the remaining three wells of the AlgiMatrix™ 3D Culture System plate received completely fresh medium in the amount of 2 ml per well. Twenty SCID mice (n=20) each received $1 \times 10^6$ CAPAN-1 cancer cells. Growth of the cancer cells was monitored by bioluminescence imaging. FIG. 12 shows a representative example of cancer cells proliferating in a SCID mouse and in the prototype as represented by the bioluminescence signal progressively increasing over a 28-day time period. FIG. 12 also compares cancer cell growth of the prototypes vs. the SCID mice vs. the AlgiMatrix™ 3D Culture System plate. Cancer cell proliferation in the prototypes was similar to that observed in SCID mice. Of note, the three prototype replicates in prototypes were similar as indicated by the small error bars shown in the log scale graph, while cancer cell proliferation in the SCID mice was highly variable. As expected and as shown in FIG. 13, cancer cells cultured in the conventional AlgiMatrix™ 3D Culture System plate quickly exhausted their nutrient supply and died by day 7.

Example 2

The novel device has the ability to assess prolonged anti-tumor effects.

Figure 14:
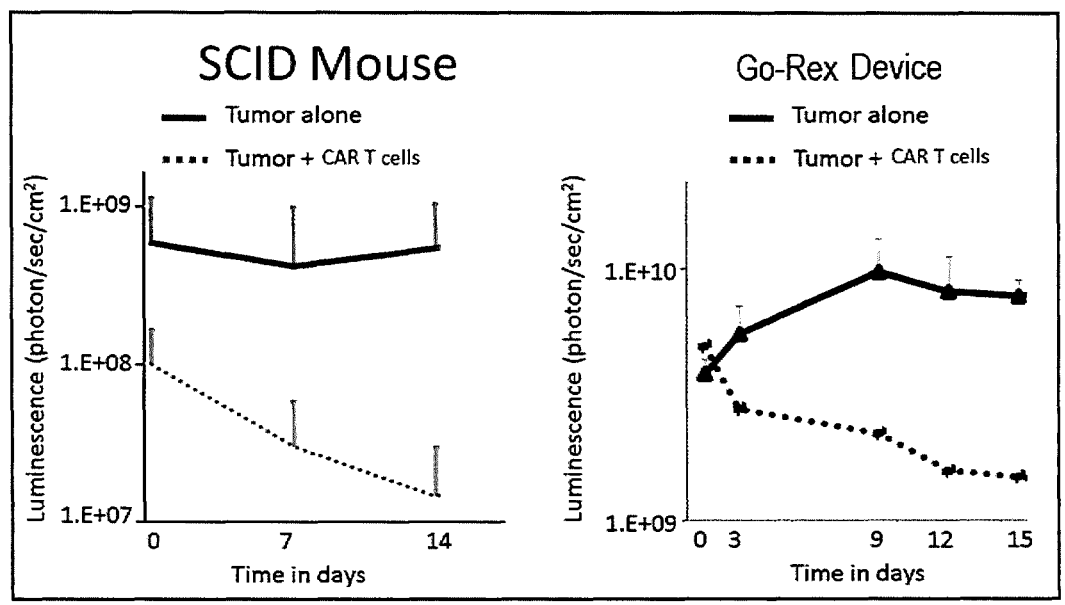
FIG. 14 shows how CAR T cell administration in SCID mice resulted in a decrease in tumor signal which was sustained for a period of two weeks and shows how the same anti-tumor effects was seen when CAR T cells were added directly to a test prototype of the present invention.

To determine whether the anti-tumor effects of T cells that were genetically engineered to include chimeric antigen receptors (CAR T) cells could be measured in the present invention with similar sensitivity and specificity as that achieved in SCID mice, three prototypes of the configuration in Example 1 were engrafted with $1 \times 10^6$ CAPAN1 cancer cells. XX SCID mice were also engrafted with $1 \times 10^6$ CAPAN-1 cancer cells. Post engraftment, $20 \times 10^6$ CAR T cells were added to each prototype and injected into each SCID mouse. As shown in the left hand panel of FIG. 14, CAR T cell administration in SCID mice resulted in a decrease in tumor signal which was sustained for a period of two weeks, indicating the infused CAR T cells were killing the CAPAN-1 cancer cells and were thus able to produce anti-tumor effects. The right hand panel of FIG. 14 shows how the same anti-tumor effects was seen when CAR T cells were added directly to the prototype. This demonstrates how the novel prototype can be a suitable surrogate to SCID mice, thereby allowing researchers to rely more frequently upon use of an in vitro device instead of SCID mice.

Example 3

The present invention can allow chemokine gradients to be established throughout the device.

Figure 15:
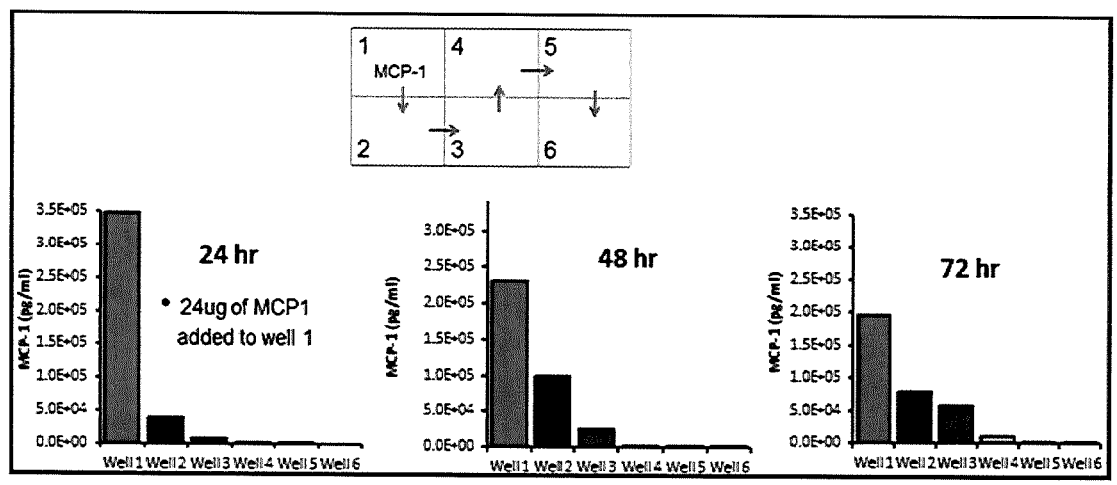
FIG. 15 shows now the present invention can allow chemokine gradients to be established throughout the device.

A prototype test device was configured with six compartments. Each compartment had a square bottom with a 12 cm² surface area. Walls allowed medium to reside directly above the bottom of each compartment at a height of 5 cm. The compartments were arranged three compartments long and two compartments in a similar pattern to a traditional six well plate. Small passage openings between various adjoining walls of the compartments allowed chemokine to move between compartments. The openings were approximately 2 mm×2 mm and at the base of the center of the walls between connected compartments. The top panel of FIG. 15 shows arrows indicating the expected gradient path created by the passages between compartments. In essence, the design was a maze pattern intended to allow the device to be moved (e.g., into an incubator) without causing a disruption of the chemokine gradient. To test whether the novel design supported the generation of a gradient, one compartment (designated as well #1 in FIG. 15) of the device was spiked with 24 ug of recombinant MCP1. Next, the chemokine concentrations were determined in wells 1 through 6 at 24, 48 and 72 hours. The bottom panel of FIG. 15 shows the concentration of MCP1 in the different wells at the indicated time points. As expected, MCP1 levels progressively decreased in well 1 over time and became detectable in an increasing fashion in compartments along the path allowed by passages. For example, the compartments designated in FIG. 15 as #2 (24 hours), #3 (48 hours) and #4 (72 hours) showed increasing amounts of MCP1 and a gradient could be clearly seen at 72 hours. This shows that the present invention can support the generation of a chemokine gradient and suggests the device can be used to produce a chemokine gradient that will reach T cells located in a distant well. T cells in that distant well can then be assessed in terms of their response.

Example 4

Data indicate the present invention can be used to distinguish between first and second generation CAR T cells.

Figure 16:
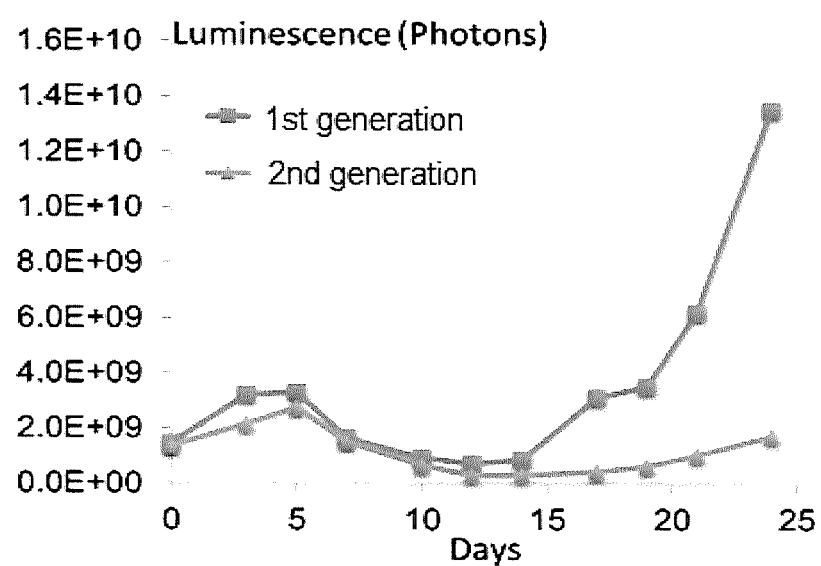
FIG. 16 shows that data indicate the present invention can be used to distinguish between first and second generation CAR T cells.

The prototype design of Example 3 was used to evaluate the ability to target pancreatic cancer cells. 60 ml of medium was present in each well. Results are shown in FIG. 16. A culture of luminescence CAPAN-1 cancer cells was established in compartment 6 in each of two prototypes. First generation CAR T cells were placed in compartment number 1 of each of one prototype. Second generation CAR T cells were placed in compartment number 1 of the other prototype. In both prototypes, CAR T cells followed the chemokine gradient expressed by the CAPAN-1 cancer cells (migration data not shown) and reached the CAPAN-1 cancer cells. Initially, both first and second generation CAR T variants demonstrated the ability to decrease cancer cell luminescence, suggesting they were equally effective at killing the CAPAN-1 cancer cells and it appeared that on about Day-12 the cancer cells were nearly eliminated. However, thereafter the second generation CAR T cells began to show dramatically better persistence and were able to continue anti-tumor activity while the first generation CAR T cells lost their cancer killing capacity and the cancer cells were able to recover. It is important to note that with conventional in vitro devices it would not be possible to distinguish between these CAR T generations for two important reasons. First, conventional in vitro devices do not allow migration and must initiate the experiment with the T cells in the same compartment as the cancer cells. Second, as shown previously, conventional in vitro devices cannot sustain cultures for more than two days (see FIG. 13) because there are not enough nutrients for cells to survive. Therefore, the T cell attack on the cancer cells cannot be monitored for a long enough period of time to detect critical differences in killing capacity over time. Using conventional methods, scientists would likely only learn of the differences by using SCID mice, thereby wasting time and money getting the critical knowledge that can quickly and inexpensively be obtained by the present invention. Of note the Example also demonstrates how the use of gas permeable material can allow medium exchange to be eliminated for at least up to 28 days. In the case of experiments performed in Example 3, no medium was exchanges as there was enough medium present in the device (i.e. 6 compartments at 60 ml per compartment=360 ml).

Skilled artisans are encouraged to recognize that for very short term experiments of cell migration over short distances, it may be more cost effective to create a device that does not rely on the use of gas permeable material or upon larger medium volumes. In such case, a device with at least two compartments should be configured with a passage between the compartments to allow signals and cells to pass from compartment to compartment. However, as shown in Example 4, the use of gas permeable material can allow medium exchange to be eliminated for at least up to 28 days.

Those skilled in the art will recognize that numerous modifications can be made thereof without departing from the spirit of the present disclosure. Therefore, it is not intended to limit the breadth of the invention to the embodiments illustrated and described. Rather, the scope of the invention is to be interpreted by the appended claims and their equivalents. Each publication, patent, patent application, and reference cited herein is hereby incorporated herein by reference in its entirety.

What is claimed is:

1. A cell culture apparatus comprising:
   at least a first compartment, a second compartment, and a third compartment, each compartment separated from adjacent compartments by a common wall with each compartment including a gas permeable bottom and adapted to hold medium at a volume to bottom footprint ratio of at least 2, each common wall including one permanently open passage, wherein the permanently open passage is an opening through the common wall, connecting the bottom of the adjacent compartments that allows the contents of the compartment to communicate with another compartment, and not including medium mixing equipment, medium perfusion equipment, or gas pumping equipment and wherein the bottoms of the compartments and the bottom of the open passages are in a common horizontal plane.

2. The apparatus of claim 1 wherein the gas permeable bottoms are comprised of silicone.

3. The apparatus of claim 1 including a removable lid.

4. The apparatus of claim 1 wherein at least one compartment includes a matrix.

5. The apparatus of claim 4 wherein the matrix is attached to the bottom.

6. The apparatus of claim 4 wherein the matrix is not a solid sub stance.

7. The apparatus of claim 1 wherein at least one wall of at least one compartment is tinted in color.

8. The apparatus of claim 1 wherein the bottom of at least one compartment is tinted in color.

9. The apparatus of claim 1 wherein the bottom of at least one compartment is square.

10. The apparatus of claim 1 wherein the bottom of at least one compartment is textured.

11. The apparatus of claim 3 wherein the removable lid does not allow a gap for gas transfer to the compartments.

12. The apparatus of claim 1, wherein at least one passage is a slot that forms a complete break in the wall between two compartments.

13. The apparatus of claim 1 wherein the apparatus is circular when viewed from the top.

14. The apparatus of claim 1 wherein at least one passage includes a closure that can be opened or closed.

15. The apparatus of claim 1 wherein there are 6 compartments.

16. The apparatus of claim 1 wherein there is only one passage between each compartment.

17. The apparatus of claim 1 wherein the gas permeable bottom is hydrophobic.

18. The apparatus of claim 1 wherein the ratio of the volume of medium to the surface area of the bottom ratio is from 2 to 15.

19. The apparatus of claim 1 wherein the compartments are not symmetrical.

* * * * *